United States Patent [19]

Rodewald

[11] Patent Number: 5,220,086
[45] Date of Patent: Jun. 15, 1993

[54] CATALYTIC PROCESSES IN THE PRESENCE OF ZEOLITES OF INCREASED INTERNAL ACID ACTIVITY AND DECREASED EXTERNAL ACID ACTIVITY

[75] Inventor: Paul G. Rodewald, Rocky Hill, N.J.

[73] Assignee: Mobil Oil Corporation, Fairfax, Va.

[21] Appl. No.: 803,867

[22] Filed: Dec. 9, 1991

Related U.S. Application Data

[63] Continuation-in-part of Ser. No. 540,723, Jun. 21, 1990, abandoned.

[51] Int. Cl.$^5$ .................. C07C 15/00; C07C 5/22; B01J 29/06; B01J 21/16
[52] U.S. Cl. ................... 585/407; 585/415; 585/470; 585/700; 502/71; 502/77; 502/81; 502/83; 502/85
[58] Field of Search ............... 585/407, 415, 470, 700; 502/71, 77, 81, 83, 85

[56] References Cited

U.S. PATENT DOCUMENTS

| | | | |
|---|---|---|---|
| 3,591,488 | 7/1971 | Eberly, Jr. et al. | 208/111 |
| 4,117,026 | 9/1978 | Haag et al. | 260/671 |
| 4,469,806 | 9/1984 | Forbus et al. | 502/62 |
| 4,477,583 | 10/1984 | Rodewald | 502/71 |
| 4,552,648 | 11/1985 | Rosinski et al. | 208/120 |
| 4,654,454 | 3/1987 | Barri et al. | 585/417 |
| 4,670,614 | 6/1987 | Ushio et al. | 585/417 |
| 4,670,620 | 6/1987 | Jacobs et al. | 585/640 |
| 4,954,243 | 9/1990 | Kuehl et al. | 585/653 |

*Primary Examiner*—Anthony McFarlane
*Assistant Examiner*—Nhat D. Phan
*Attorney, Agent, or Firm*—Alexander J. McKillop; Malcolm D. Keen; Marina V. Schneller

[57] ABSTRACT

The invention relates to the treatment of crystals of ZSM-5 with mineral acid to produce ZSM-5 crystals which have an acid activity associated with the pores and channels thereof, the shape selective portion of the crystal, which is greater than the acid activity of the non-shape selective portion of the crystal or the surface of the ZSM-5 crystal, and the effect of the treated zeolite, as a catalyst component, in catalytic hydrocarbon conversions.

4 Claims, No Drawings

{ 5,220,086 }

CATALYTIC PROCESSES IN THE PRESENCE OF ZEOLITES OF INCREASED INTERNAL ACID ACTIVITY AND DECREASED EXTERNAL ACID ACTIVITY

CROSS REFERENCE TO RELATED APPLICATIONS

This application is a continuation-in-part of copending application Ser. No. 07/540,723 which was filed on Jun. 21, 1990, now abandoned, which is relied upon and incorporated by reference herein.

FIELD OF THE INVENTION

The invention relates to a catalyst which exhibits decreased selectivity for coke make during shape selective catalytic conversion. That is, in the shape selective catalysis, in the presence of the catalyst of the invention much lower coke makes are achieved. Reduction in coke make translates into improved cycle length and improved product yield.

In upgrading aromatization of aliphatic hydrocarbons containing $C_2$–$C_{10}$ carbon atoms to higher molecular weight products, the catalyst provides a catalysis of increased selectivity and absolute yield for BTX (benzene toluene and xylene(s). As recognized in the art, BTX is a valuable high octane booster. Moreover, the xylenes, including o-, m-, and p-xylene, are valuable chemical commodities in the production of plastics. In aromatization of paraffins, containing $C_2$–$C_{10}$ carbon atoms, the catalyst provides a catalysis of increased selectivity for toluene, which in turn can be subjected to toluene disproportionation conditions to produce xylene(s).

The invention involves treatment of zeolites with mineral acid to produce zeolites which have an increased acid activity associated with the pores and channels thereof, the shape selective portion of the crystal, and decreased acid activity associated with the non-shape selective portion of the crystal or the surface of the zeolite.

Decreased external activity of zeolite catalysts reduces generally undesirable, non-shape selective surface reactions and by-products resulting from non-shape selective catalysis. Enhanced internal activity catalysts offer potential process improvements such as lower operating temperature, lower aging rate, and higher space velocity for greater through-put. The improvement of the invention resides in decreasing external surface activity and the non-shape selective reactions which occur at the surface of the zeolite, while simultaneously maintaining or enhancing internal activity and the shape selective reactions which occur within the pores of the zeolite.

BACKGROUND OF THE INVENTION

For many decades, acidic clays and amorphous silica-alumina compositions have been used to catalyze the cracking of carbon-carbon bonds, for alkene isomerization and polymerization, aromatic alkylation with alkenes or alcohols, transalkylation, and other acid-catalyzed reactions. The cracking of alkanic bonds requires the highest activity; alkene transformations require lower catalytic strength and/or lower temperature. In the presence of those amorphous porous materials, the catalysis was not shape selective.

ZSM-5 is a porotectosilicate, a microporous crystalline silicate. It is identified by its X-ray diffraction pattern which was described in U.S. Pat. No. 3,702,886, which is relied upon and incorporated by reference herein. It is referred to as a shape selective zeolite. Its shape selective function can be quantified by a test known as the Constraint Index, described below. The shape selectivity is attributed to the pores and channels within the crystal. On the basis of pore size and pore window dimensions, organic compounds or hydrocarbon feeds are provided with constrained access to, and egress from, the internal portion of the crystal. Accordingly, the nature, particularly the size, of molecules which can be subjected to shape selective conversion and of the product(s) which can be produced thereby are controlled or limited by the pore size and pore window dimension of the specific zeolite used in the shape selective catalysis.

Reactions which occur at the surface, rather than within the pores and channels, of the ZSM-5 crystal are not bound by size constraints provided by the pore size and pore window dimensions of the zeolite and, accordingly, tend to be comparable in results to those results produced by amorphous materials used in the past.

The activity of a catalyst comprising ZSM-5 is based inter alia on its acidity. Acidity of a zeolite is a function of the aluminum content of the zeolite. Often the acidity of the zeolite can be gleaned from the determined framework silica:alumina mole ratio.

Various acid catalyzed shape selective reactions can be effected in the presence of the zeolite. These include hydrocarbon cracking, toluene disproportionation, xylene isomerization, alkene conversion, alkene oligomerization, alkene isomerization and methanol conversion (e.g. to gasoline) Cf. W. O. Haag et al, "The active site of acidic aluminosilicate catalysts," pages 589–591, NATURE, Vol. 309 (June 1984).

External acid activity, at the surface of the zeolite crystal, is detrimental to overall selectivity of the shape selective catalytic reactions undertaken in the presence of the zeolite. Accordingly, and for example, in propylene oligomerization to lube range olefins, external surface acid activity is poisoned using bulky organic amines in order to obtain the desired selectivity to near linear lube range olefins.

Zeolite acid activity, sometimes referred as the alpha value, can be increased by various means such as mild steaming, hydrothermal treatment in the presence of alumina, and vapor phase treatment with aluminum chloride. However, such procedures increase acid activity non-selectively and result in materials with increased internal and external acid activity. That increased external acid activity is detrimental to the extent it augments non-shape selective catalyzed product distribution.

SUMMARY OF THE INVENTION

The invention relates to providing ZSM-5 which exhibits two acid activities. More particularly, the product ZSM-5 of the invention is provided with an acid activity for shape selective catalysis which exceeds the activity of the ZSM-5 for non-shape selective catalysis.

The process of the invention consists essentially of a one step process which has unexpected effects on catalyst external/internal acid activity. The process of the invention produces the unexpected result of increasing the acid activity of the shape selective function of the ZSM-5 while simultaneously decreasing the acid activity of the non-shape selective function of the ZSM-5.

The process comprises a low temperature treatment of the ZSM-5 under acidic conditions, effective to increase its catalytic cracking activity while reducing its activity for dealkylation of 1,3,5-tri-t-butylbenzene.

The process results in a catalyst which exhibits decreased selectivity for coke make during shape selective catalytic conversion. That is, in the shape selective catalysis, in the presence of the catalyst of the invention much lower coke makes are achieved. Reduction in coke make translates into improved cycle length and improved product yield.

In aromatization of paraffins, containing $C_2$-$C_{10}$ carbon atoms, the catalyst provides a catalysis of increased selectivity and absolute yield for BTX (benzene toluene and xylene(s)). As recognized in the art, BTX is a valuable high octane booster. Moreover, the xylenes, including o-, m-, and p-xylene, are valuable chemical commodities in the production of plastics. In aromatization of paraffins, containing $C_2$-$C_{10}$ carbon atoms, the catalyst provides a catalysis of increased selectivity for toluene, which in turn can be subjected to toluene disproportionation conditions to produce xylene(s).

DETAILED DESCRIPTION OF THE INVENTION

In accordance with the invention, a catalyst is provided which exhibits good aromatization properties. In particular, the invention relates to aromatization of $C_2$-$C_{10}$ paraffins to $C_6$ and $C_{6+}$ aromatics, in the presence of the catalyst. The paraffins are alkanes and alkenes of $C_2$ to $C_{10}$ carbon atoms. Preferably, the aromatics are BTX. When the process of the invention exhibits high selectivity for the production of toluene, the process of the invention further includes disproportionation of toluene to xylene(s) and preferably to p-xylene.

The conditions for converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20. Conditions for converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20.

Disproportionating product toluene to a product comprising benzene and xylenes is undertaken at reaction conditions including a temperature of from about 200° C. to about 760° C., a pressure of from about atmospheric to about 60 atmospheres and a weight hourly space velocity of from about 0.08 to about 50.

As noted above, the aromatizations can be undertaken at reduced coke make and increased aromatic product selectivity over a catalyst comprising ZSM-5 which exhibits an acid activity for shape selective catalysis which exceeds the activity of the ZSM-5 for non-shape selective catalysis. The zeolite has an increased acid activity associated with the pores and channels thereof, the shape selective portion of the crystal, and decreased acid activity associated with the non-shape selective portion of the crystal or the surface of the zeolite. These two different characteristics of the ZSM-5 product of the invention will be discussed below in terms of dealkylation of the 1,3,5-tri-t-butylbenzene and its acid or catalytic racking activity.

Dealkylation of the 1,3,5-tri-t-butylbenzene is an acid catalyzed reaction that occurs at the surface of the ZSM-5 crystal and not within the pores or channels of the ZSM-5. On account of the molecular size of the 1,3,5-tri-t-butylbenzene, the ZSM-5 does not allow constrained access of that molecule to the intracrystalline pores and/or channels of the crystal. Accordingly, dealkylation of 1,3,5-tri-t-butylbenzene catalyzed by the ZSM-5 is not attributable to shape selective catalysis occurring within the pores or channels of the ZSM-5.

Dealkylation of 1,3,5-tri-t-butylbenzene was carried out at 250° C. and atmospheric pressure. A solution of 6.27% 1,3,5-tri-t-butylbenzene and 93.73% toluene was pumped over 0.10 g catalyst at a total weight hourly space velocity of 40. Products were analyzed by gas chromatography. The $k_{TTBB}$ rate constants were calculated using the following equation.

$$k_{TTBB} = \frac{\text{Catalyst Density (g/cc)} \times \text{Gas Flow/cc/min) ln}(1 - \epsilon)}{60 \text{ sec/min} \times \text{Catalyst WT (g)}}$$

where $\epsilon$ is the fractional conversion.

The ZSM-5 product of the invention exhibits substantially reduced activity for dealkylation of 1,3,5-tri-t-butylbenzene. The reduced activity of the ZSM-5 for dealkylation of the 1,3,5-tri-t-butylbenzene is measured by comparison of the rate of the precursor and product ZSM-5 for 1,3,5-tri-t-butylbenzene dealkylation. Unexpectedly, the ZSM-5 product of the invention exhibits increased shape-selective acid catalyzed cracking activity; if the sole criterion for dealkylation of 1,3,5-tri-t-butylbenzene were acid activity, the acid catalyzed cracking activity of the product ZSM-5 of the invention is sufficient to cause increased dealkylation over that realized in the presence of the precursor ZSM-5.

The acid catalyzed cracking activity is measured as the Alpha Value. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

For the purposes of this invention the rate constant ratio alpha/$k_{TTBB}$ after acid treatment is greater than the alpha/$k_{TTBB}$ ratio before acid treatment.

The zeolite ZSM-5 and its identification by X-ray diffraction pattern is described in U.S. Pat. No. 3,702,886, which is relied upon and incorporated by reference herein. The zeolite ZSM-5 has a framework silica:alumina mole ratio of at least 12. The zeolite ZSM-5 has a constraint index which ranges from 1 to 12 depending on the temperature of measurement.

The method by which Constraint Index is determined is described fully in U.S. Pat. No. 4,016,218, incorporated herein by reference for details of the method. Constraint Index (CI) values for some typical zeolites including some which are suitable as catalysts in the process of this invention are:

| CI (at test temperature) | |
|---|---|
| ZSM-4 | 0.5 (316° C.) |
| ZSM-5 | 6-8.3 (371° C.-316° C.) |
| ZSM-11 | 5-8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index is an important and even critical definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 12 or less, depending on the temperature employed during the test method within the range of 290° C. to about 538° C., with accompanying conversion between 10% and 60%, the CI may vary within the indicated range of 12 or less. Accordingly, it will be understood to those skilled in the art that the CI as utilized herein, while affording a highly useful means for characterizing the zeolites of interest, is approximately taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

In accordance with the process of the invention, the reactant ZSM-5 material has a framework silica:alumina mole ratio of at least 12. Usually it is in the hydrogen form. The hydrogen form may be generated in-situ, e.g., when an acid is used for the treatment. Another way to convert it to hydrogen form, is to ion-exchange it with a source of ammonium ion, and then calcining the ammonium exchanged form.

Acidic treatment of the ZSM-5 in accordance with the invention is undertaken under mild conditions for a time sufficient to cause the rate of the dealkylation of 1,3,5-tri-t-butylbenzene in the presence of the product acid treated ZSM-5 to be less than the rate of dealkylation in the presence of the reactant ZSM-5. Decrease in the dealkylation rate is directly dependent on loss of framework aluminum at sites on the surface(s) of the ZSM-5 crystal(s).

The acidic treatment of the ZSM-5 is undertaken in the presence of an aqueous solution of a mineral acid usually at the reflux temperature of the acidic solution, at ambient conditions of pressure. The acidic treatment can be undertaken at temperatures lower than reflux temperature with an increase in treatment time. The acidic treatment can also be undertaken at elevated pressure with a subsequent increase in reflux temperature and decrease in treatment time.

The normality of the acid solution can range from $10^{-7}$ to the normality of the concentrated acid. Mineral acids including phosphoric, hydrochloric, nitric or sulfuric acid can be used as the acidic reagent in the process.

After treatment the ZSM-5 is subjected to washing (e.g. with distilled water) to remove residual acid and then dried and thereafter calcined. In the examples below calcination is undertaken in air at 2° C./minute to 538° C. and then maintained at 538° C. for four hours.

Typical replacing cations would include hydrogen, ammonium and metal cations including mixtures of the same. Of the replacing metallic cations, particular preference is given to cations of metals such as rare earth metals, manganese and calcium, as well as metals of Group II of the Periodic Table, e.g., zinc, and Group VIII of the Periodic Table, e.g., platinum and nickel.

Typical ion exchange techniques include contacting the members of the family of zeolites with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251 and 3,140,253.

After metal ion exchange the zeolites are washed with water and dried at a temperature ranging from 150° to about 600° and thereafter calcined in air or other inert gas at temperatures ranging from about 150° to about 600° F. and thereafter calcined in air or other inert gas at temperatures ranging from about 500° to about 1500° for periods of time ranging from 1 to 48 hours.

Ion exchange of the crystalline silicate materials can be conducted to effect ammonium exchange at acidic sites of said materials. The source of the ammonium ion is not critical; thus the source can be ammonium hydroxide or an ammonium salt such as ammonium nitrate, ammonium sulfate, ammonium chloride and mixtures thereof. These reagents are usually in aqueous solutions; by way of illustration, aqueous solutions of 1N $NH_4OH$, 1N $NH_4NO_3$, 1N $NH_4Cl$ and 1N $NH_4Cl/NH_4OH$ have been used to effect ammonium ion exchange on these, and similar materials. The pH of the ion exchange is not critical but generally maintained at 7 to 12. Ammonium exchange may be conducted for a period of time ranging from about 0.5 to about 20 hours at a temperature ranging from ambient up to about 100° C. The ion exchange may be conducted in multiple stages. Calcination of the ammonium exchanged will produce the crystalline silicate or zeolite in its acid form. Calcination can be effected at temperatures up to about 600° C.

In the case of many catalysts, it is desired to incorporate the zeolite ZSM-5 hereby prepared with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjunction with the zeolite ZSM-5, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good physical strength, because in petroleum refinery processing, the catalyst is often subjected to conditions which tend to break the catalyst down into powder-like materials which cause problems in processing.

Naturally occurring clays which can be composited with the hereby synthesized zeolite ZSM-5 include the montmorillonite an kaolin families which include the sub bentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite ZSM-5 catalyst hereby synthesized can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline silicate and inorganic oxide gel matrix vary widely with the crystalline silicate content ranging from about 0.1 to about 90 percent by weight, and more usually in the range of about 10 to about 70 percent by weight of the composite.

As noted in the parent application, in general, organic compounds such as, for example, those selected from the group consisting of hydrocarbons, alcohols and ethers, are converted to conversion products such as, for example, aromatics and lower molecular weight hydrocarbons, over the catalytically active form of the composition of this invention by contact under organic compound conversion conditions including a temperature of from about 100° C. to about 800° C. a pressure of from about 0.1 atmosphere (bar) to about 200 atmospheres, a weight hourly space velocity of from about 0.08 hr$^{-1}$ to about 2000 hu$^{-1}$ and a hydrogen/feedstock organic compound mole ratio of from 0 (no added hydrogen) to about 100.

Such conversion processes include, as non-limiting examples, cracking hydrocarbons to lower molecular weight hydrocarbons with reaction conditions including a temperature of from about 300° C. to about 800° C., a pressure of from about 0.1 atmosphere (bar) to about 35 atmospheres and a weight hourly space velocity of from about 0.1 to about 100; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 50; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components to product enriched in p-xylene with reaction conditions including a temperature from about 230° C. to about 510° C., a pressure of from about 1 atmospheres to about 35 atmospheres, a weight hourly space velocity of from about 0.1 to about 200 and a hydrogen/hydrocarbon mole ratio of from about 0 to about 100; disproportionating toluene to product comprising benzene and xylenes with reaction conditions including a temperature of from about 200° C. to about 760° C., a pressure of from about atmospheric to about 60 atmospheres and a weight hourly space velocity of from about 0.08 to about 50; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

EXAMPLES

Example 1

Samples of ZSM-5 having silica-alumina ratios of 70/1 and 31/1 were treated overnight in refluxing 1N nitric acid, filtered, washed with distilled water, dried at 110° C., and program calcined in air at 2° C./minute to 538°, then 4 hours at 538° C.

Internal catalyst activity was measured by alpha determination. External catalyst activity was measured by dealkylation of 1,3,5-tri-t-butylbenzene. A comparison of the results is reported in Table I:

TABLE I

| Activity | HZSM-5 $SiO_2:Al_2O_3 = 70$ | | HZSM-5 $SiO_2:Al_2O_3 = 31$ | |
|---|---|---|---|---|
| | Fresh | $HNO_3$ treated | Fresh | $HHNO_3$ treated |
| alpha | 136 | 628 | 493 | 1800 |
| $k_{TTBB}$ | 1.09 | 0.82 | 0.53 | 0.22 |

Clearly, the $HNO_3$ treatment substantially increased internal alpha and decreased external $k_{TTBB}$ activity.

Example 2

Propane conversion was carried out over 0.50 g HZSM-5 at 550° C., 0 psig, and 1.0 WHSV. Results are shown in Table 2. Propane conversion was also carried out over 0.50 g HZSM-5 which had been treated with nitric acid as described in Example 1. Operating conditions were 535° C., 0 psig, and 1.0 WHSV. Results are shown in Table 2.

TABLE 2

Propane Conversion Over HZSM-5 and Acid Treated HZSM-5

| | HZSM-5 | Acid Treated HZSM-5 |
|---|---|---|
| Temperature, °C. | 550 | 535 |
| Pressure, psig | 0 | 0 |
| WHSV | 1.0 | 1.0 |
| Conversion, wt. % | 72 | 72 |
| Product Distribution, wt. % | | |
| Methane | 34.5 | 32.5 |
| Ethane | 24.3 | 24.4 |
| Ethylene | 6.6 | 3.6 |
| Propylene | 4.3 | 3.5 |
| i-Butane | 0.9 | 1.3 |
| n-Butane | 1.4 | 1.7 |
| Butenes | 0.8 | 0.8 |
| $C_5$ | 0.2 | 0.1 |
| $C_6$ | 0.1 | 0.1 |
| $C_7$ | 0.1 | 0.0 |
| Benzene | 7.2 | 7.7 |
| Toluene | 12.7 | 15.7 |
| Xylenes | 6.6 | 8.0 |
| $C_9^+$ Aromatics | 0.3 | 0.6 |
| | 100.0 | 100.0 |

The product distributions are properly compared at equivalent 72% conversions. The untreated catalyst attained 72% conversion at 550° C., whereas the acid treated catalyst attained 72% conversion at a lower 535° C. This lower operating temperature indicates a desirably longer cycle length for the acid treated catalyst.

The conversion of propane to high octane and petrochemically valuable aromatics is a highly desirable property for a catalyst. The aromatics yield (selectivity × conversion) for the untreated catalyst was 19%, whereas the aromatics yield for the acid treated catalyst was 23% corresponding to an increase of 21%.

Both catalytic runs were terminated at 29 hours on stream. At this point the untreated catalyst showed 25% conversion, while the acid treated catalyst showed a substantially higher 44% conversion despite its lower 535° C. operating temperature. This improved conversion performance is due to the increased internal acid activity of the acid treated zeolite and to the decreased external acid activity of the acid treated zeolite leading to reduced deactivation from coke formation.

The % coke on both catalysts was determined at 29 hours on stream. The untreated catalyst showed 7.25% coke. The acid treated catalyst showed a significantly lower 4.23% coke corresponding to a 42% reduction in coke make. This reduced coke make is due to the decreased external acid activity of the zeolite and translates into improved cycle length and product yield.

What is claimed is:

1. A process for converting a feedstream comprising an aliphatic hydrocarbon containing at least 2 carbon atoms to a product of higher molecular weight than the aliphatic comprising contacting the feedstream with a catalyst at a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20, and recovering said product of higher molecular weight, wherein the catalyst consists essentially of a silicate exhibiting the X-ray diffraction pattern of ZSM-5, in acid form, wherein the silicate is formed by a method consisting essentially of the steps of providing as a reactant an aluminosilicate exhibiting the X-ray diffraction pattern of ZSM-5 wherein said reactant exhibits an alpha value which is effective to crack hydrocarbons under cracking conditions and exhibits an activity to dealkylate 1,3,5-tri-t-butylbenzene, as measured by the rate of dealkylation of 1,3,5-tri-t-butylbenzene in the presence of said reactant;

treating the reactant, in hydrogen form, with a solution of nitric acid at reflux temperature or lower; and recovering said silicate, which silicate exhibits an alpha value greater than that of said reactant and a rate for dealkylation of 1,3,5-tri-t-butylbenzene which is less than that rate of dealkylation of 1,3,5-tri-t-butylbenzene by said reactant.

2. A process for converting a feedstream comprising an aliphatic containing at least 2 carbon atoms to a product of higher molecular weight than the aliphatic comprising contacting the feedstream with a catalyst at a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20, and recovering said product, which contains an aromatic fraction in which the aromatics are $C_8+$ aromatics; wherein the catalyst consists essentially of a silicate exhibiting the X-ray diffraction pattern of ZSM-5, in acid form, wherein the silicate is formed by a method consisting essentially of the steps of providing as a reactant an aluminosilicate exhibiting the X-ray diffraction pattern of ZSM-5 wherein said reactant exhibits an alpha value which is effective to crack hydrocarbons under cracking conditions and exhibits an activity to dealkylate 1,3,5-tri-t-butylbenzene, as measured by the rate of dealkylation of 1,3,5-tri-t-butylbenzene in the presence of said reactant;

treating the reactant, in hydrogen form, with a solution of nitric acid at reflux temperature or lower; and recovering said silicate, which silicate exhibits an alpha value greater than that of said reactant and a rate for dealkylation of 1,3,5-tri-t-butylbenzene which is less than that rate of dealkylation of 1,3,5-tri-t-butylbenzene by said reactant.

3. In a process for aromatizing a $C_{2+}$ aliphatic hydrocarbon stream in the presence of a catalyst which comprises ZSM-5 which becomes coked and deactivated during a catalytic aromatization cycle, the improvement comprising reducing production of coke, and increasing product yield by contacting said $C_{2+}$ aliphatic hydrocarbon with a zeolite catalyst, in acid form, consisting of a silicate exhibiting the X-ray diffraction pattern of ZSM-5, and recovering a product effluent which comprises benzene, toluene, and at least one xylene selected from the group consisting of o-xylene, m-xylene, and p-xylene, wherein the silicate is formed by a method consisting essentially of the steps of providing as a reactant an aluminosilicate exhibiting the X-ray diffraction pattern of an ZSM-5 wherein said reactant exhibits an alpha value which is effective to crack hydrocarbons under cracking conditions and exhibits an activity to dealkylate 1,3,5-tri-t-butylbenzene, as measured by the rate of dealkylation of 1,3,5-tri-t-butylbenzene in the presence of said reactant;

treating the reactant, in hydrogen form, with a solution of nitric acid at reflux temperature or lower; and recovering said silicate;

which silicate exhibits an alpha value greater than that of said reactant and a rate for dealkylation of 1,3,5-tri-t-butylbenzene which is less than that rate of dealkylation of 1,3,5-tri-t-butylbenzene by said reactant.

4. The process of claim 3, further comprising the step of subjecting the toluene to disproportionation conditions to produce xylene.

* * * * *